US012414917B2

United States Patent
Davis et al.

(10) Patent No.: US 12,414,917 B2
(45) Date of Patent: Sep. 16, 2025

(54) OPIOID INDEPENDENT SURGICAL ANESTHETIC

(71) Applicant: UNIVERSITY OF UTAH RESEARCH FOUNDATION, Salt Lake City, UT (US)

(72) Inventors: Brett Davis, Salt Lake City, UT (US); Andrew M. Simpson, Salt Lake City, UT (US); Jayant P. Agarwal, Salt Lake City, UT (US); Jill E. Shea, Salt Lake City, UT (US); Himanshu Jayant Sant, Salt Lake City, UT (US); Bruce K. Gale, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 102 days.

(21) Appl. No.: 17/683,687

(22) Filed: Mar. 1, 2022

(65) Prior Publication Data

US 2023/0000772 A1 Jan. 5, 2023

Related U.S. Application Data

(63) Continuation-in-part of application No. PCT/US2020/050727, filed on Sep. 14, 2020.
(Continued)

(51) Int. Cl.
*A61K 9/127* (2025.01)
*A61K 9/00* (2006.01)
(Continued)

(52) U.S. Cl.
CPC ............ *A61K 9/127* (2013.01); *A61K 9/0019* (2013.01); *A61K 9/1277* (2013.01); *A61K 31/445* (2013.01); *A61K 47/36* (2013.01)

(58) Field of Classification Search
CPC .... A61K 9/127; A61K 9/0019; A61K 9/1277; A61K 31/445; A61K 47/36; A61K 9/0014; A61K 9/06; A61K 9/5123
See application file for complete search history.

(56) References Cited

U.S. PATENT DOCUMENTS 4,889,740 A * 12/1989 Price .................. A23D 9/00
426/606
5,227,165 A 7/1993 Domb et al.
(Continued)

FOREIGN PATENT DOCUMENTS

CN 103816111 A 5/2014
CN 107496382 A 12/2017
(Continued)

OTHER PUBLICATIONS

Charlotte Martin, Andy De Baerdemaeker, Jan Poelaert, Annemieke Madder, Richard Hoogenboom, Steven Ballet. (2016). Controlled-release of opioids for improved pain management. Materials Today, 19(9),491-502. doi.org/10.1016/j.mattod.2016.01.016. (Year: 2016).*
(Continued)

*Primary Examiner* — Marianne C Seidel
*Assistant Examiner* — Amanda Michelle Petritsch
(74) *Attorney, Agent, or Firm* — Workman Nydegger

(57) ABSTRACT

An opioid independent surgical anesthetic composition includes an injectable dosage form of a hydrogel having a plurality of solid lipid matrix particles entrapped therein. The solid lipid matrix particles include a lipophilic local anesthetic drug and a lipid glyceride (e.g., saturated triglyceride or lipid blend of various lipid glycerides). Methods for creating a long-acting local anesthetic product can include creating a bulk solid of a lipid matrix product by heating a lipid solvent above its melting point, dissolving a lipophilic local anesthetic drug therein, reducing a temperature of the resultant drug-lipid solution to below the melting point of
(Continued)

the lipid solvent, and heat annealing the lipid matrix to remove or reduce presence of any unstable polymorphs in the lipid matrix. The methods can further include crushing the bulk solid of the lipid matrix product to form solid lipid matrix particles and entrapping the solid lipid matrix particles within a hydrogel.

23 Claims, 10 Drawing Sheets

Related U.S. Application Data

(60) Provisional application No. 63/156,799, filed on Mar. 4, 2021, provisional application No. 63/014,788, filed on Apr. 24, 2020, provisional application No. 62/900,369, filed on Sep. 13, 2019.

(51) Int. Cl.
  *A61K 9/1277* (2025.01)
  *A61K 31/445* (2006.01)
  *A61K 47/36* (2006.01)

(56) References Cited

U.S. PATENT DOCUMENTS

| | | | |
|---|---|---|---|
| 9,283,283 | B2 | 3/2016 | Giammona et al. |
| 9,421,198 | B2 | 8/2016 | Bourdon et al. |
| 9,655,991 | B2 | 5/2017 | Gousse et al. |
| 9,782,490 | B2 | 10/2017 | Tauzin |
| 10,098,961 | B2 * | 10/2018 | Wiebensjo ............ A61Q 19/08 |
| 2003/0152634 | A1 | 8/2003 | Bodmeier |
| 2008/0279944 | A1 * | 11/2008 | Sawhney ............ A61K 9/1647 424/484 |
| 2010/0266693 | A1 | 10/2010 | Evans et al. |
| 2011/0171310 | A1 | 7/2011 | Gousse et al. |
| 2014/0039061 | A1 | 2/2014 | Wiebensjö et al. |
| 2014/0256695 | A1 | 9/2014 | Nguyen et al. |
| 2016/0228613 | A1 | 8/2016 | Gavard Molliard |
| 2016/0346433 | A1 | 12/2016 | Bon et al. |
| 2017/0172961 | A1 | 6/2017 | Heller et al. |
| 2018/0186900 | A1 | 7/2018 | Mitragotri et al. |

FOREIGN PATENT DOCUMENTS

| | | |
|---|---|---|
| EP | 3294355 A1 | 3/2018 |
| EP | 3315130 A1 | 5/2018 |

OTHER PUBLICATIONS

Li, L. C., Zhu, L., Song, J. F., Deng, J. S., Bandopadhyay, R., & Wurster, D. E. (2005). Effect of Solid State Transition on the Physical Stability of Suspensions Containing Bupivacaine Lipid Microparticles. Pharmaceutical Development and Technology, 10(2), 309-318. https://doi.org/10.1081/PDT-54475 (Year: 2005).*
Bagshaw, Kyle R., et al. "Pain management via local anesthetics and responsive hydrogels." Therapeutic delivery, vol. 6, Issue 2, Feb. 2015, pp. 165-176.
Miyamoto, Kenji, et al. "Evaluation of in vivo biocompatibility and biodegradation of photocrosslinked hyaluronate hydrogels (HADgels)." Journal of Biomedical Materials Research Part A: An Official Journal of the Society for Biomaterials, The Japanese Society for Biomaterials, and the Australian Society for Biomaterials and the Korean Society for Biomaterials, vol. 70, Issue 4, 2004, pp. 550-559.
Shipton, Edward A. "New formulations of local anaesthetics—part I." Anesthesiology research and practice, 2012, vol. 2012, Article ID 546409, 11 pages.
Zhang et al., "Local anesthetic lidocaine delivery system:chitosan and hyaluronic acid-modified layer-by-layer lipid nanoparticles", Drug Deliv, 2016, vol. 23, No. 9, pp. 3529-3537.
Albertini et al., "Novel multifunctional platforms for potential treatment of cutaneous wounds: Development and in vitro characterization", Int J Pharm, vol. 440, No. 2, Jun. 9, 2012, pp. 238-249.
Davis et al., "Entrapping bupivacaine-loaded emulsions in a crosslinked-hydrogel increases anesthetic effect and duration in a rat sciatic nerve block model", Int J Pharm, vol. 588, Jul. 30, 2020.
International Search Report and Written Opinion received for PCT Patent Application No. PCT/US2020/050727, mailed on Dec. 21, 2020, 9 pages.
Jia et al., "Prolongation of sciatic nerve blockade by in situ cross-linked hyaluronic acid", Biomaterials, vol. 25, No. 19, 2004, pp. 4797-4804.
Lemoine et al., "Effect of long-chain triglyceride lipid emulsion on bupivacaine-induced changes in electrophysiological parameters of rabbit Purkinje cells", Fundam Clin Pharmacol., Oct. 2014, vol. 28, No. 5, pp. 481-488.

* cited by examiner

OPIOID INDEPENDENT SURGICAL ANESTHETIC

CROSS-REFERENCE TO RELATED APPLICATIONS

This application claims priority to and the benefit of U.S. Provisional Patent Application No. 63/156,799, filed Mar. 4, 2021, and entitled OPIOID INDEPENDENT SURGICAL ANESTHETIC. This application is also a "bypass" continuation-in-part application of PCT Patent Application No. PCT/US20/50727, filed Sep. 14, 2020 and entitled "OPIOID INDEPENDENT SURGICAL ANESTHETIC, which claims priority to and the benefit of each of U.S. Provisional Patent Application No. 63/014,788, filed Apr. 24, 2020 and entitled "HYALURONIC ACID HYDROGEL ANESTHETIC DRUG DELIVERY SYSTEM" and U.S. Provisional Patent Application No. 62/900,369, filed Sep. 13, 2019 and entitled "HYALURONIC ACID HYDROGEL ANESTHETIC DRUG DELIVERY SYSTEM." Each of the foregoing applications is incorporated herein by reference in its entirety.

STATEMENT REGARDING FEDERALLY SPONSORED RESEARCH

This invention was made with government support under grant no. 1946204 awarded by the National Science Foundation. The government has certain rights in the invention.

BACKGROUND

Technical Field

The present application relates to anesthetic compositions and methods for creating the same. More particularly, the present application relates to long-acting, opioid independent anesthetics that may be used to manage postoperative pain.

Relevant Technology

Medical practitioners often employ surgical techniques to treat injuries and disorders. Surgical techniques often involve manipulating or structurally altering a patient's body by—or through—an incision. Even after closing a surgical incision (e.g., with a suture), patients may be subject to postoperative pain at the surgical site, such as acute pain immediately following the surgical operation and/or lingering pain as the surgical site heals.

Many postoperative pain treatment regimens involve the use of opioids as a centrally-acting analgesic to mitigate the pain. For example, members of a surgery or recovery team may administer an initial dose or doses of opioids to a patient after a surgical procedure, and the patient may be prescribed additional doses of opioids for self-administration to maintain analgesia as the effects of the initial dose(s) wear off. The freedom to self-medicate opioids leads some patients to over-medicate or otherwise abuse the use of their prescribed drugs, often leading to opioid addiction or even an overdose. The risks and dangers of opioid addiction and overdosing have gained significant attention in recent years, particularly due to the pervasiveness of opioid addiction within the U.S. and many other countries around the globe.

In some instances, rather than administering an initial opioid dose, medical practitioners administer a local anesthetic to a surgical site in an effort to treat postoperative pain. However, conventional local anesthetics often only provide analgesia at the surgical site for a few hours following administration. It is time consuming and impractical to administer iterative doses of local anesthetic, and because many local anesthetics are delivered via injection, there is an inherent additional risk of infection. These obstacles and the ease by which centrally acting opioid medications can be administered orally (e.g., as a pill or capsule) contribute to the continued prescription of opioids to treat postoperative pain—despite the personal and social harms clearly linked with their widespread use.

Alternative pain management strategies are needed to reduce the dependence on opioids for treating postoperative pain. For example, new or alternative local anesthetics are needed that can temporally extend the analgesic effect at a surgical site following administration. However, there is a dearth in the market for such products, and existing products that purport to provide long-acting local analgesia suffer from a number of shortcomings, such as a failure to perform as reported, high cost, complicated drug delivery procedures, and unfavorable drug release profiles.

Accordingly, there are a number of problems and disadvantages with existing postoperative pain management regimens and opioid independent surgical anesthetics that can be addressed.

BRIEF SUMMARY

Various embodiments disclosed herein are related to systems, methods, components, apparatuses, and kits associated with opioid independent surgical anesthetics. Such embodiments may beneficially improve postoperative pain management and may mitigate the need for centrally-acting opioid medication after a surgical procedure by, for example, facilitating long-acting, local analgesia at a surgical site.

A first aspect provides an opioid independent surgical anesthetic composition. The opioid independent surgical anesthetic composition includes an injectable dosage form of a hydrogel that has a plurality of solid lipid matrix particles entrapped therein. The plurality of solid lipid matrix particles includes a lipophilic local anesthetic drug and a lipid glyceride, such as a saturated glyceride (e.g., a saturated triglyceride or a lipid blend of mono, di, or triglycerides). In some instances, the opioid independent anesthetic composition is provided as part of a kit within a ready-to-use syringe.

In some embodiments, the hydrogel is a hyaluronic acid hydrogel. In an embodiment, the hyaluronic acid hydrogel may be crosslinked, or not crosslinked. Furthermore, in some instances, the lipophilic local anesthetic drug is (or includes) bupivacaine and the saturated triglyceride is (or includes) tristearin. Other amide based anesthetics could also be used (e.g., ropivacaine, lidocaine, etc.), as could other lipid glycerides. In one aspect, the plurality of solid lipid matrix particles substantially include glycerides (e.g., triglycerides or a lipid blend) forming a β-phase crystalline state. The solid lipid matrix may additionally, or alternatively, have a melting point greater than about 45° C., preferably greater than about 70° C., and/or each of the plurality of solid lipid matrix particles has a longest dimension of about 200 μm or less.

In another aspect, an opioid independent surgical anesthetic composition includes a ready-to-use injectable dosage form of a hyaluronic acid hydrogel (e.g., crosslinked or not crosslinked) having lipid emulsion droplets containing bupivacaine, ropivacaine, or another amide based anesthetic (e.g., any -'caine anesthetic) entrained therein. The opioid independent surgical anesthetic composition is configured to release the anesthetic in a biphasic manner when administered at a surgical site. The biphasic release may include a burst phase and a sustained release phase, improving postoperative pain management in an opioid independent fashion. In some embodiments, for example, between 30%-70% of the ropivacaine, bupivacaine or other anesthetic is cumulatively released from the hydrogel during the burst phase (e.g., the burst phase may be between 8-24 hours post administration), and between 70%-99% of the ropivacaine, bupivacaine or other anesthetic is cumulatively released from the hydrogel by 72 hours post administration. In other words, after the burst phase, the remaining 30-70% may be released in a window 8-72 hours, or 24-72 hours after administration.

In another aspect, a method for creating an opioid independent surgical anesthetic composition includes (i) creating a bulk solid of a lipid matrix product by heating a lipid solvent above a melting point of the lipid solvent, dissolving a lipophilic local anesthetic drug into the lipid solvent to form a drug-lipid solution, and quenching or otherwise reducing a temperature of the drug-lipid solution to below the melting point of the lipid solvent; (ii) forming solid lipid matrix particles by crushing the bulk solid of the lipid matrix product; and (iii) entrapping a plurality of size-selected solid lipid matrix particles within a hydrogel.

In some embodiments, creating the bulk solid of the lipid matrix product also includes performing a heat annealing process, e.g., after quenching or otherwise reducing the temperature of the drug-lipid solution to below the melting point of the lipid solvent. The heat annealing process can include, for example, maintaining a temperature of the drug-lipid solution at approximately 8° C.-12° C. below the melting point of the lipid solvent for a period of time. Thus, the drug-lipid solution may be quickly quenched to ambient temperature or below, and afterwards heated again during the heat annealing process.

Furthermore, in some embodiments, the lipophilic local anesthetic drug includes ropivacaine or bupivacaine, the lipid solvent includes a lipid blend, a saturated triglyceride, or other lipid glyceride, and the hydrogel includes a hyaluronic acid hydrogel (crosslinked or not). Additionally, or alternatively, each of the plurality of size-selected solid lipid matrix particles has a longest dimension less than about 200 μm.

In an embodiment, an opioid independent surgical anesthetic composition may comprise an injectable dosage form of a hydrogel having a plurality of solid lipid matrix particles entrapped therein, the plurality of solid lipid matrix particles comprising a lipophilic local anesthetic drug and a saturated glyceride.

In an embodiment, the saturated glyceride comprises a lipid blend including one or more of a monoglyceride, a diglyceride, or a triglyceride. For example, a lipid blend may include one or more monoglycerides in combination with one or more diglycerides, and/or one or more triglycerides. In an embodiment, the lipid blend may include monoglyceride(s) and diglyceride(s), monoglyceride(s) and triglyceride(s), diglyceride(s) and triglyceride(s), or monoglyceride(s), diglyceride(s), and triglyceride(s). In an embodiment, the blend includes at least some monoglyceride(s) or diglyceride(s), e.g., in addition to any triglyceride(s). As used herein, lipid blend refers to a blend of two or more different lipid components (e.g., monoglycerides, diglycerides, and/or triglycerides). In an embodiment, such a lipid blend includes at least one monoglyceride and/or at least one diglyceride (i.e., it is not just solely triglycerides). Such monoglycerides, diglycerides, and any included triglycerides may be saturated.

In an embodiment the saturated glyceride comprises a saturated triglyceride.

In an embodiment the hydrogel comprises a hyaluronic acid hydrogel.

In an embodiment the hyaluronic acid is included in an amount from 0.5% to 3% by weight.

In an embodiment the hyaluronic acid has a molecular weight in a range from 500,000 to 3,000,000 Da.

In an embodiment the lipophilic local anesthetic drug comprises at least one amide based anesthetic.

In an embodiment the plurality of solid lipid matrix particles substantially comprises triglycerides or other glycerides forming a β-phase crystalline state.

In an embodiment the solid lipid matrix particles have a melting point greater than about 45° C., or greater than about 70° C.

In an embodiment the solid lipid matrix particles are comprised of one or more of monoglycerides, diglycerides, or triglycerides with carbon chain lengths of 12 to 22 carbon atoms.

In an embodiment each of the plurality of solid lipid matrix particles has a longest dimension of about 200 μm or less.

In an embodiment the local anesthetic drug has a concentration relative to the solid matrix lipid particle of from 1% to 50% by weight.

In an embodiment the local anesthetic drug has a concentration relative to the composition as a whole that is from 0.5% to 10% by weight.

In an embodiment the solid lipid matrix particles have a density within the composition as a whole that is from 25 mg/mL to 300 mg/mL.

In an embodiment the composition consists essentially of the injectable dosage form that is ready-to-use, the composition being a hyaluronic acid hydrogel having a liposomal emulsion containing bupivacaine, ropivacaine, lidocaine, or another amide based local anesthetic entrained therein.

In an embodiment the composition is configured to release bupivacaine, ropivacaine, lidocaine, or another amide based local anesthetic in a biphasic manner when administered at a surgical site, the biphasic release comprising a burst phase and a sustained release phase, wherein:
(i) between 30%-70% of the bupivacaine, ropivacaine, lidocaine, or another amide based local anesthetic is cumulatively released from the hydrogel during the burst phase between 8-24 hours post administration, and/or
(ii) between 70%-99% of the bupivacaine, ropivacaine, lidocaine, or another amide based local anesthetic is cumulatively released from the hydrogel by 72 hours post administration.

An embodiment is directed to a method for creating a long-acting local anesthetic product, comprising: creating a bulk solid of a lipid matrix product by: heating a lipid solvent above a melting point of the lipid solvent; dissolving a lipophilic local anesthetic drug into the lipid solvent to form a drug-lipid solution; reducing a temperature of the drug-lipid solution to below the melting point of the lipid solvent; and heat annealing the lipid matrix to remove or reduce presence of any unstable polymorphs in the lipid matrix; forming solid lipid matrix particles by crushing the bulk solid of the lipid matrix product; and entrapping a plurality of the solid lipid matrix particles within a hydrogel.

In an embodiment, creating the bulk solid of the lipid matrix product comprises quenching the drug-lipid solution to ambient temperature or below when reducing the temperature of the drug-lipid solution to below the melting point of the lipid solvent, such quenching being followed by the heat annealing, wherein the heat annealing comprises heating and maintaining a temperature of the lipid matrix at approximately 8° C.-12° C. below the melting point of the lipid solvent for approximately one hour or longer.

In an embodiment the lipophilic local anesthetic drug comprises bupivacaine, ropivacaine, lidocaine, or another amide based local anesthetic.

In an embodiment the lipid solvent comprises a lipid blend (e.g., as described above or elsewhere herein).

In an embodiment the hydrogel comprises a cross-linked or non-cross-linked hyaluronic acid hydrogel.

An embodiment is directed to a method for administering an opioid independent surgical anesthetic composition, the composition comprising an injectable dosage form of a hydrogel having a plurality of solid lipid matrix particles entrapped therein, the plurality of solid lipid matrix particles comprising a lipophilic local anesthetic drug and a saturated glyceride, the method comprising topically applying the composition to a surgical or other wound bed, or injecting the composition via any of various routes.

In an embodiment the composition is injected or otherwise delivered into an intrathecal space, an intra-articular space, another fluid-filled cavity, an ocular space, injected or otherwise delivered transdermally, orally, subcutaneously, intranasally, vaginally, buccally, epidurally, dentally, intratumorally, intramuscularly, or intravenously, on its own or in combination with another therapeutic agent.

Features from any of the disclosed embodiments may be used in combination with one another, without limitation. For example, any of the compositional or other limitations described with respect to one embodiment may be present in any of the other described embodiments. In addition, other features and advantages of the present disclosure will become apparent to those of ordinary skill in the art through consideration of the following detailed description and the accompanying drawings.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Figure 1A:
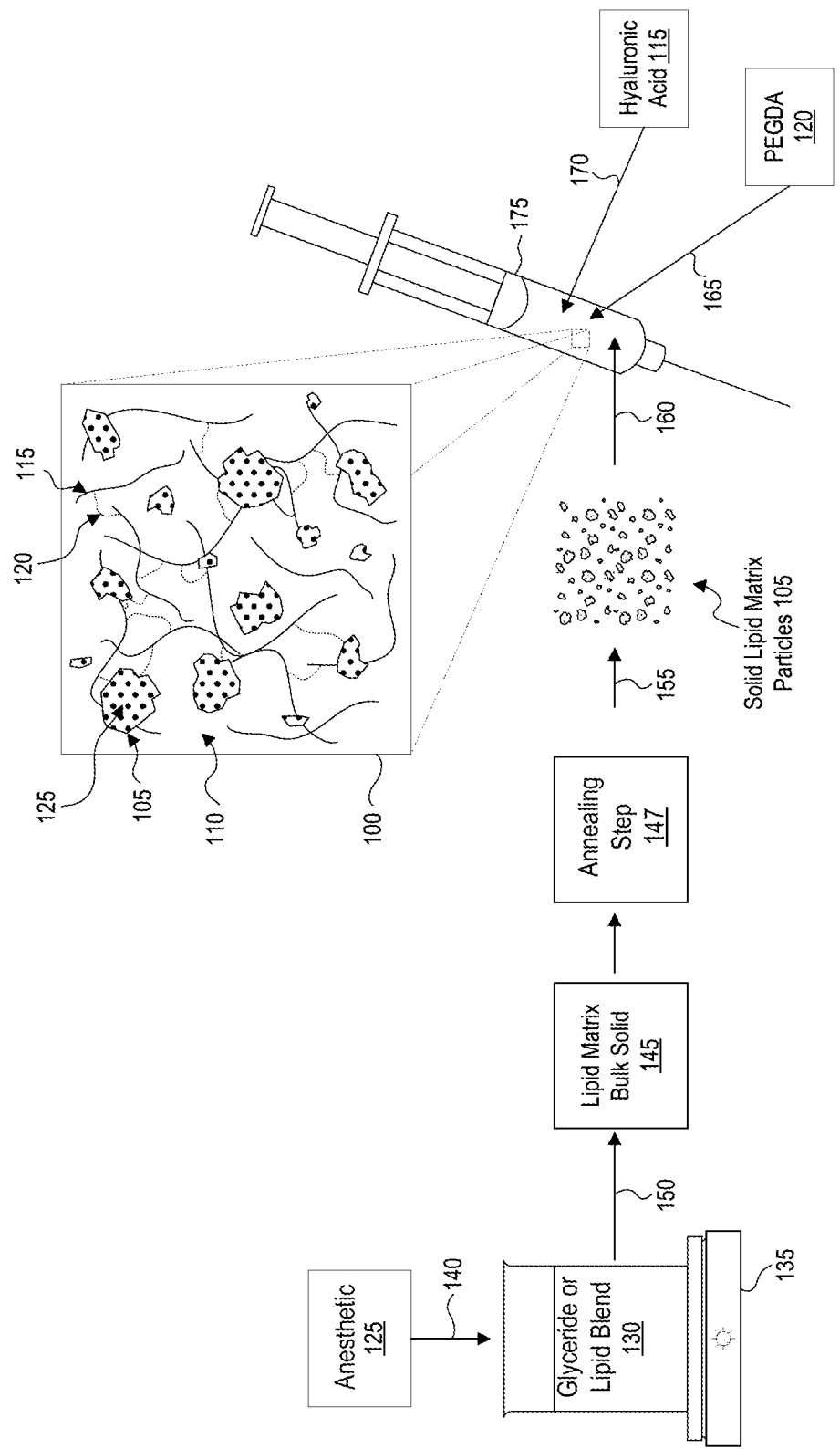
FIGS. 1A-1B illustrate schematic representations of an opioid independent surgical anesthetic composition that includes solid lipid matrix particles entrapped within a hydrogel and schematic representations of a procedure for manufacturing the opioid independent surgical anesthetic composition, in accordance with one or more embodiments of the present disclosure.

As used in the specification, a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise. In addition, unless otherwise indicated, numbers expressing quantities, constituents, distances, or other measurements used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

By way of further example, use of the terms "about," "approximately," "substantially," or the like used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition.

As used herein, the term "between" is inclusive of any endpoints noted relative to a described range. For example, a recited range of between 30% and 70% includes both 30% and 70%.

Exemplary Opioid Independent Surgical Anesthetics

As indicated above, alternative pain management strategies are needed to reduce the dependence on opioids for treating postoperative pain. However, existing products that purport to provide long-acting local anesthetic effects are deficient in many respects. For example, one purported extended-release local anesthetic preparation—Exparel® (Pacira, Parsippany, NJ)—is a liposomal bupivacaine suspension. Although Exparel® has shown some promise in reducing the quantity of opioids required for maintaining analgesia after surgery, there have been concerns about its true efficacy and duration of effect in reducing post-operative pain (e.g., as demonstrated by independent clinical trials). Exparel® is also cumbersome to use, requiring the administering physician to repeatedly jab the patient with a needle to deliver subcutaneous injections of the liposomal bupivacaine suspension around the periphery of the wound (or surgical site). This process is also time consuming, taking the physician approximately 10 minutes in the operating room to administer all of the requisite injections.

Additionally, Exparel® typically fails to provide a burst effect of drug release following injection, making Exparel® unsuitable for managing acute pain at a surgical site immediately following a surgical procedure. To address this issue, Pacira, the manufacturer of Exparel® recommends mixing the liposomal bupivacaine with standard bupivacaine (e.g., bupivacaine HCl) prior to infiltration, or separately injecting standard bupivacaine at the surgical site (e.g., with a separate syringe) in conjunction with Exparel®. Using Exparel® in conjunction with standard bupivacaine further adds to the complexity, time, and/or cost associated with implementing Exparel® for postoperative pain management and underscores its inability to provide sufficient analgesia at the injection site without additional anesthetics.

These concerns, coupled with the high cost of Exparel®, have led to significant concerns about the cost utility and efficacy of Exparel®.

As noted above, Exparel® comprises liposomal bupivacaine. Liposomes may experience accelerated release of their contents in vivo due to disruptive serum protein adsorption to the lipid bilayer and by retardation of electrostatic potential by salts/ions in the physiologic milieu. Such reactions to in vivo conditions may be a cause of the failure of liposomal bupivacaine to satisfy the needs of medical practitioners for a long-acting local anesthetic. Other attempts to create lipid micro/nano-particle bupivacaine sustained release systems have failed due to instability, poor drug loading, and/or rapid drug expulsion during storage. For example, unstable α-phase lipid polymorphs may spontaneously transition to the thermodynamically favored β-phase and expel loaded drugs during the phase transition.

Accordingly, there exists a long-felt need for an improved opioid independent, long-acting local anesthetic formulation that provides, for example, prolonged analgesia following administration (e.g., 48 hours or longer, such as 72 hours or longer), that can be administered in a simple, non-time-consuming manner (e.g., as a ready-to-use composition deliverable through a conventional syringe), and that demonstrates an initial burst release of anesthetic followed by localized, sustained release of anesthetic to address both the acute and lingering postoperative pain—all preferably at an affordable price.

Various embodiments disclosed herein are related to systems, methods, components, apparatuses, and kits associated with opioid independent surgical anesthetics. In one example embodiment, an opioid independent surgical anesthetic composition includes an injectable dosage form of a hydrogel that has a plurality of solid lipid matrix particles entrapped therein. The plurality of solid lipid matrix particles includes a lipophilic local anesthetic drug and a glyceride, such as a saturated triglyceride or lipid blend of lipid glycerides (e.g., including mono, di, and/or triglycerides). In another example embodiment, an opioid independent surgical anesthetic composition includes a ready-to-use injectable dosage form of a hyaluronic acid hydrogel having lipid emulsion droplets containing bupivacaine entrained therein. In an embodiment, the hyaluronic acid may not be cross linked with a crosslinker (e.g., PEGDA). In other embodiments, it may be crosslinked.

Those skilled in the art will recognize, in view of the present disclosure, that at least some of the disclosed embodiments may address various shortcomings and/or problems associated with conventional techniques and products for managing postoperative pain.

For example, at least some anesthetic compositions of the present disclosure utilize a hydrogel, such as a hyaluronic acid hydrogel, as a carrier to facilitate drug delivery (at least some anesthetic compositions of the present disclosure may be generalized as hyaluronic acid local anesthetics (HA-LAs), such as a lipid emulsion HALA or a lipid matrix particle HALA). Although hyaluronic acid hydrogels exhibit a gel-like consistency, hyaluronic acid hydrogels also exhibit shear-thinning mechanical properties, enabling a HALA to be injected through a small-gauged needle (e.g., 18 G-25 G) similar to standard local anesthetics prepared as an aqueous solution (or other liquid form). Unlike plain bupivacaine, which has the consistency of water, a HALA reforms into a stable gel following injection through a syringe. This allows a HALA to be applied topically, avoiding complicated and/or repetitive subcutaneous injection procedures. For example, at the end of a surgical procedure, medical practitioners may easily apply a HALA within the wound and suture the wound closed over the HALA, disposing local anesthetic directly at the source of the pain. The drug then elutes from the carrier hyaluronic acid hydrogel to provide a local analgesic effect safely and reliably. It should be appreciated that the gel-like consistency of the hydrogel advantageously allows it to conform to the wound bed as the surgical site is closed. This acts to provide anesthetic across the surface area of the wound and more efficiently direct its analgesic effects to the disrupted tissue where the pain and inflammation is more intense or originating from.

In addition, at least some HALAs of the present disclosure are configured to provide a high-rate burst drug release upon administration to a surgical site followed by a low-rate prolonged drug release. In this regard, a HALA of the present disclosure may address both acute pain that immediately follows a surgical procedure as well as lingering pain experienced as a surgical site heals. Accordingly, at least some HALAs of the present disclosure provide medical practitioners with a single product that manages both acute postoperative pain and lingering postoperative pain (e.g., in contrast with existing products that require complicated admixing procedures prior to drug administration or contemporaneous administration of multiple drug products).

In some instances, a HALA implements bupivacaine as an anesthetic agent, which is known to be cardiotoxic. Notwithstanding the cardiotoxic properties of bupivacaine, the controlled release characteristics of the HALAs of the present disclosure may enable HALAs to include a high concentration of bupivacaine relative to conventional products (e.g., 1.5% or greater w/v bupivacaine compared to 0.5% w/v for bupivacaine HCL and 1.33% w/v Exparel®) while still safely providing superior analgesic effects without risk of cardiotoxicity. In another embodiment, the anesthetic agent may be ropivacaine. Another embodiment may include lidocaine. Ropivacaine and/or lidocaine may be less cardiotoxic, e.g., given its shorter carbon chain on the amine portion of the molecule. For example bupivacaine includes a 4-carbon chain length on the amine portion of the molecule, while ropovacaine includes a 3-carbon chain length, and lidocaine includes two 2-carbon chains attached to the nitrogen atom.

The manufacturing protocol and materials for creating at least some of the HALAs of the present disclosure are simple and/or inexpensive, particularly when compared with the manufacturing protocol and materials for creating existing products that attempt to provide long-acting local anesthetic effects. In addition, HALA products of the present disclosure may be provided to medical practitioners in a shelf-stable and ready-to-use syringe (e.g., 5 cc or 10 cc) that is operable to manage both immediate postoperative pain (via an initial burst drug release) and lingering postoperative pain (via a subsequent sustained drug release) with a single application. It should be appreciated that the disclosed HALA products are beneficially shelf-stable, allowing for extended storage periods without loss of desired therapeutic effect. Accordingly, a HALA of the present disclosure may allow medical practitioners to avoid complicated admixing procedures, multiple injection procedures, contemporaneous administration of multiple anesthetic drugs (e.g., Exparel® and bupivacaine HCL), and/or other drawbacks associated with existing local anesthetics that attempt to provide long-acting effects.

In some embodiments, lipid matrix particle HALAs implement solid lipid matrix particles formed under controlled heating/cooling conditions that allow for heat annealing of the lipid melt used to form the solid lipid matrix particles. Heat annealing may advantageously remove unstable polymorphs from the lipid melt in preparation for pulverization to form the solid lipid matrix particles for entrapment within a hyaluronic acid hydrogel. In some instances, the removal of unstable polymorphs contributes to the stable and predictable diffusion-controlled drug release from lipid matrix particle HALAs.

Because the HALAs of the present disclosure may facilitate extended local control of pain at a surgical site, the HALAs of the present disclosure may provide a postoperative pain management alternative that mitigates or avoids the use of centrally-acting opioids for pain management (particularly self-administered opioids). In this regard, the HALAs of the present disclosure may help patients to avoid any potential opioid dependency, overdose, and/or addiction by allowing medical practitioners to treat a surgical site with an opioid-independent, effective, safe, and long-acting local anesthetic.

Although the present disclosure focuses in some respects on topical applications of HALAs within human patients, those skilled in the art will recognize, in view of the present disclosure, that these implementations are provided as examples only and are in no way limiting of the present disclosure. For example, a user may inject a HALA subcutaneously as a nerve blocking agent and/or on an animal subject in accordance with implementations of the present disclosure.

Furthermore, although the present disclosure focuses, in some respects, on HALAs that implement ropivacaine or bupivacaine as an anesthetic agent, a HALA may implement additional or alternative anesthetic agents, such as lidocaine or other amide based local anesthetics such as articaine, cinchocaine/dibucaine, etidocaine, levobupivacaine, lignocaine, mepivacaine, prilocaine, trimecaine, and/or others.

Having just described some of the various high-level features and benefits of the disclosed embodiments, attention will now be directed to FIGS. 1A through 9. These figures illustrate various conceptual representations, components, systems, methods, and supporting illustrations related to the disclosed embodiments.

Figure 1B:
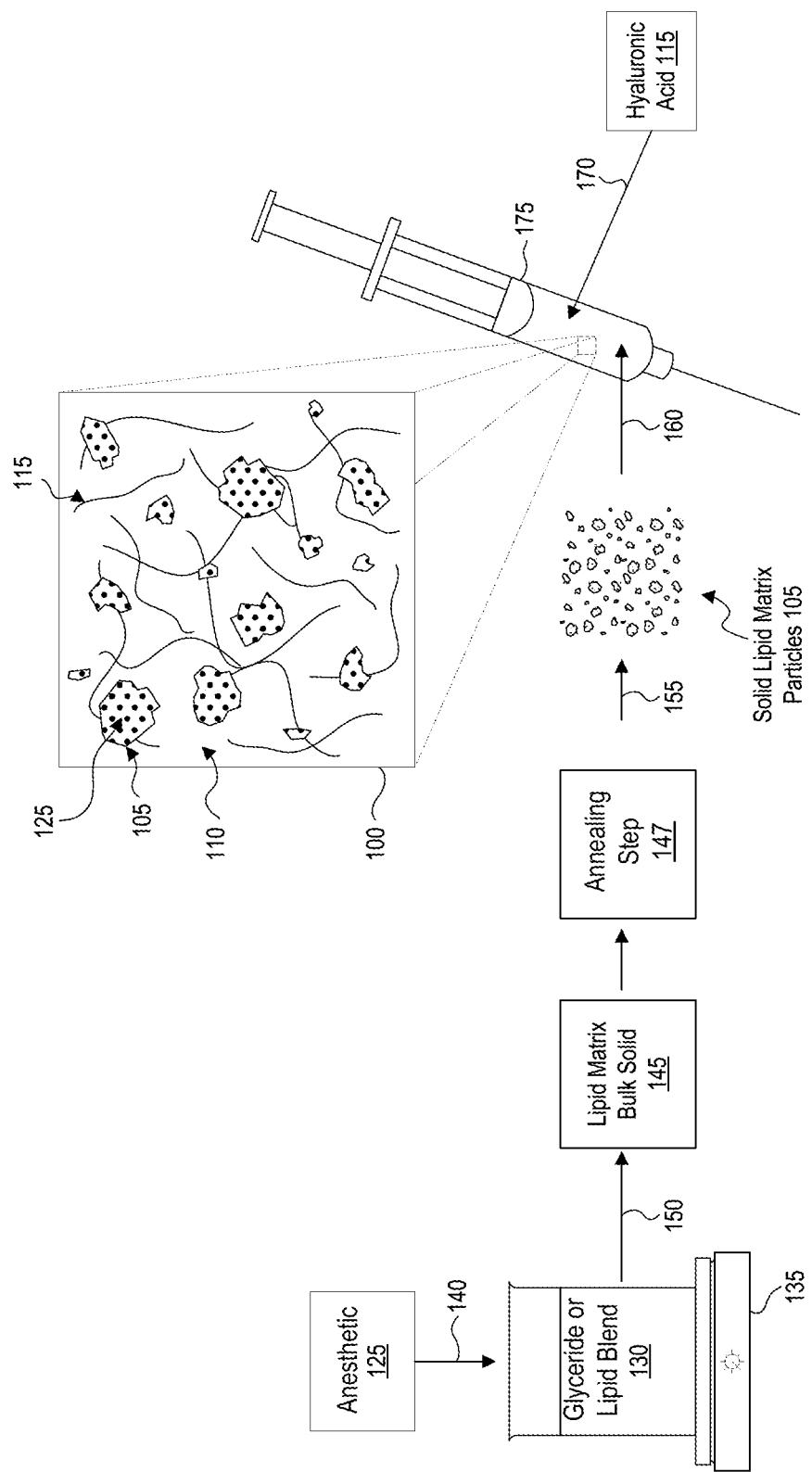

FIGS. 1A-1B illustrate a schematic representation of an opioid independent surgical anesthetic composition (i.e., lipid matrix particle HALA 100). FIGS. 1A-1B illustrates that the lipid matrix particle HALA 100 includes solid lipid matrix particles 105 entrapped within a hydrogel 110. As indicated hereinabove, in at least some embodiments, the hydrogel 110 comprises a hyaluronic acid hydrogel formed from hyaluronic acid 115. Hyaluronic acid 115 is a naturally occurring component of extracellular matrix and has demonstrated safety (e.g., a very low risk of side-effects). The hyaluronic acid may be crosslinked (with linkage 120, as shown in FIG. 1A) or not crosslinked (FIG. 1B).

In the example depicted in FIG. 1A, the hydrogel 110 is formed from thiol-modified chains of hyaluronic acid 115 that are crosslinked by thiol-reactive poly(ethylene glycol) diacrylate (PEGDA) 120 crosslinkers. The crosslinking restricts movement of the chains of hyaluronic acid 115 and forming a network structure that gives the hydrogel 110 its gel-like mechanical properties. FIG. 1B illustrates an embodiment where the hyaluronic acid 115 is not crosslinked. For example, where sufficiently high molecular weights or other properties are present, to provide the desired physical properties (e.g., sufficient viscosity, with shear thinning behavior), the crosslinking may not be needed. For example, it was found that the desired physical and mechanical properties can be achieved without need for the additional steps and ingredients required for crosslinking. Such steps are time consuming and often require less ideal chemicals. The purpose of the hyaluronic acid is simply to disperse and entrap the lipid microparticles into solution and increase viscosity for local application. Hyaluronic acid is well suited for such, because of its excellent biocompatibility, biodegradability, and shear-thinning behavior. The resulting product is viscous but also injectable through a relatively small gauge needle or other delivery head, due to its shear-thinning behavior.

As noted above, FIGS. 1A-1B also illustrate that the hydrogel 110 entraps solid lipid matrix particles 105 that are infused with a local anesthetic agent (e.g., bupivacaine, ropivacaine or other anesthetic 125 shown in FIGS. 1A-1B infused throughout solid lipid matrix particles 105 of the lipid matrix particle HALA 100). As will be described hereinafter, preliminary results indicate that the hydrogel 110 may shield at least some of the anesthetic-loaded solid lipid matrix particles 105 from harsh in vivo conditions, thereby facilitating a controlled, prolonged release of bupivacaine, ropivacaine, or other anesthetic 125 from the lipid matrix particle HALA 100 into a surgical or injection site.

FIGS. 1A-1B illustrate a schematic representation of a procedure for manufacturing the solid lipid matrix particles 105 for creating a lipid matrix particle HALA 100. FIGS. 1A-1B show that the solid lipid matrix particles 105 may, in some implementations, be formed from a combination of a lipid glyceride 130 (e.g., a lipid blend of lipid glycerides or a saturated triglyceride) and a lipophilic local anesthetic drug (e.g., bupivacaine or ropivacaine 125 illustrated in FIGS. 1A-1B above the saturated lipid or lipid blend 130). For example, the saturated lipid or lipid blend of lipid glycerides 130 may be heated (e.g., via hotplate 135 or other heating device) to a temperature above its melting point, forming a saturated glyceride lipid melt. Freebase bupivacaine, ropivacaine, or other anesthetic 125 may be dissolved into the lipid melt (indicated in FIGS. 1A-1B by arrow 140), forming a ropivacaine-lipid solution, bupivacaine-lipid solution, or other anesthetic-lipid solution.

The anesthetic-lipid solution may then be cooled to form an anesthetic-loaded lipid matrix bulk solid 145 (indicated in FIGS. 1A-1B by arrow 150). In some instances, after cooling the anesthetic-lipid solution, a heat annealing process 147 is performed. For example, a heat annealing process may include heating the material after quenching (e.g., to ambient temperature or below), and maintaining a temperature that is between about 5° C.-20° C. below the melting point of the saturated triglyceride or lipid blend of lipid glycerides 130, preferably approximately 10° C. below the melting point of the saturated triglyceride or lipid blend of lipid glycerides 130, for an extended period of time (e.g., longer than 30 minutes, preferably longer than about an hour, more preferably approximately 2 hours) as the anesthetic-lipid solution solidifies to form the anesthetic-loaded lipid matrix bulk solid 145. In an embodiment, the anesthetic is specifically ropivacaine.

Triglycerides are known to crystalize into three phases upon solidification from melt. Triglycerides may solidify into an unstable α-phase crystalline state, an intermediary β'-phase crystalline state, and/or a stable β-phase crystalline state. Other lipid glycerides (e.g., monoglycerides or diglycerides) may exhibit similar characteristics. Omitting or avoiding unstable α-phase and β'-phase crystalline structures from the anesthetic-loaded lipid matrix bulk solid 145 may increase thermodynamic stability of solid lipid matrix particles 105 formed from the anesthetic-loaded lipid matrix bulk solid 145 (e.g., which may possibly increase shelf life stability) and may contribute to the desired diffusion-controlled drug release from the lipid matrix particle HALA 100 (see FIG. 8).

Preliminary results indicate that performing the heat annealing process described herein may remove substantially all unstable α-phase and β'-phase crystalline structures from an anesthetic-loaded lipid matrix bulk solid 145, providing an anesthetic-loaded lipid matrix bulk solid 145 that substantially comprises the β-phase crystalline state. The heat annealing step 147 can be helpful in removing such undesirable polymorph structures. By way of example, attention is briefly directed to FIG. 9, which illustrates a graph of differential scanning calorimetry data of non-annealed bupivacaine-loaded lipid matrix particles (curve 910) and heat annealed bupivacaine-loaded lipid matrix particles (curve 920). As is evident from curve 910 of FIG. 9, the heat flow necessary to increase the temperature of the non-annealed bupivacaine-loaded lipid matrix particles includes significant fluctuations between about 50° C.-70° C., which indicates the presence of unstable α-phase triglyceride crystalline structures in non-annealed bupivacaine-loaded lipid matrix particles. In contrast, as is evident from curve 920 of FIG. 9, such fluctuations do not appear between about 50° C.-70° C. for heat annealed bupivacaine-loaded lipid matrix particles, indicating that unstable α-phase triglyceride crystalline structures are not present in heat annealed bupivacaine-loaded lipid matrix particles. Ropivacaine-loaded lipid matrix particles are expected to exhibit similar characteristics.

The anesthetic-loaded lipid matrix bulk solid 145 may be pulverized or crushed (e.g., with a mortar and pestle or functional equivalent) to form solid lipid matrix particles 105 in powder form (indicated in FIGS. 1A-1B by arrow 155). The solid lipid matrix particles 105 may be admixed with components for forming the hydrogel 110 (e.g., hyaluronic acid 115, optionally a crosslinker such as PEGDA 120; admixing indicated in FIG. 1A by arrows 160, 165, and 170). In some instances, the admixed solid lipid matrix particles 105, hyaluronic acid 115, and PEGDA 120 are disposed within a syringe 175 where crosslinking may complete to form a lipid matrix particle HALA 100 that is ready for immediate use by a medical practitioner in a manner that avoids bedside admixing or other complicated procedures. FIG. 1B illustrates an alternative example that does not include any PEGDA or other crosslinker, further simplifying the preparation method.

Furthermore, in some instances, the solid lipid matrix particles 105 that are size selected prior to admixing with the components for forming the hydrogel 110 (e.g., including only solid lipid matrix particles that have a longest dimension of between about 25 μm-500 μm, preferably between about 50 μm-300 μm, more preferably about 200 μm or less). For example, the solid lipid matrix particles 105 formed by pulverizing the anesthetic-loaded lipid matrix bulk solid 145 (indicated by arrow 155) may be sieved to isolate solid lipid matrix particles of different size ranges, such as 25 μm or smaller, between 25 μm and 50 μm, between 100 μm and 125 μm, etc. (e.g., using ASTM (American Society for Testing and Materials) standardized sieves with pore sizes of 25, 50, 100, and 125 μm). In some instances, drug release characteristics of a lipid matrix particle HALA 100 may be tuned/customized based on size selection of the solid lipid matrix particles 105 used to form the lipid matrix particle HALA 100.

Drug release characteristics of a lipid matrix particle HALA 100 may be customized by modifying various components, such as lipid matrix particle size (as indicated above), fatty acid chain length of the components of the lipid or lipid blend, crystallization morphology (e.g., tunable by modifying heat annealing or refraining from performing heat annealing), drug loading concentration, type and/or degree and/or mass ratio of crosslinking, and/or others. In one example, a lipid matrix particle HALA 100 includes hyaluronic acid at 1.25% w/v, where the ropivacaine, bupivacaine, or other anesthetic concentration is 2% w/v. Other configurations are within the scope of this disclosure.

In some instances, the triglyceride or lipid blend 130 used to form the solid lipid matrix particles 105 of FIGS. 1A-1B comprises a saturated lipid or lipid blend of glycerides with a melting point above room temperature (e.g., a melting point greater than about 45° C., such as about 70° C. or greater). Examples of such saturated triglycerides that may be used or included in a lipid blend include trilaurin, trimyristin, tripalmitin, tristearin, and/or others. By way of example, the carbon chain length included in the glyceride may be at least 10, at least 12, at least 14, at least 16, at least 18 carbon atoms, such as from 14 to 30, from 16 to 24, or from 18 to 22 carbon atoms. By way of example, lauryl groups have 12 carbon atoms, myrstyl groups have 14 carbon atoms, palmitic groups have 16 carbon atoms, and stearyl groups have 18 carbon atoms. Longer chain lengths may be helpful in extending release of the anesthetic over a longer period of time.

Although the discussion of FIG. 1A focuses, in at least some respects, on lipid matrix particle HALAs 100 formed with hyaluronic acid hydrogels that are crosslinked by PEGDA, other types of hydrogels and/or crosslinkers are within the scope of this disclosure. For example, a hydrogel can be crosslinked without the presence of PEGDA where the thiol-modified hyaluronan crosslinks with itself via oxidative disulfide bond formation to form hydrogels. By way of further example, as shown in FIG. 1B, no crosslinker need be present. Furthermore, as noted above, other lipophilic local anesthetic drugs aside from ropivacaine or bupivacaine are within the scope of this disclosure.

Figure 2B:
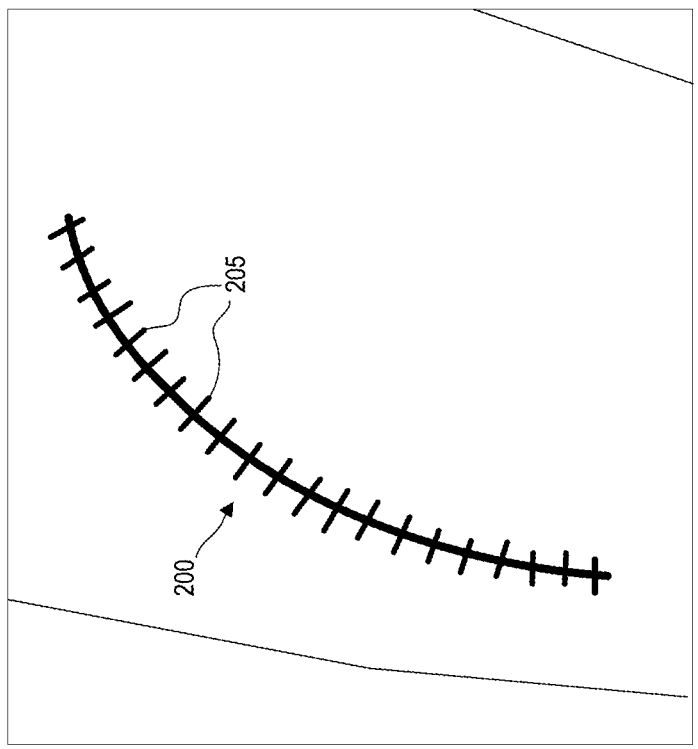
FIGS. 2A and 2B illustrate an example of applying an opioid independent surgical anesthetic composition to a surgical site, in accordance with one or more embodiments of the present disclosure.
Figure 2A:
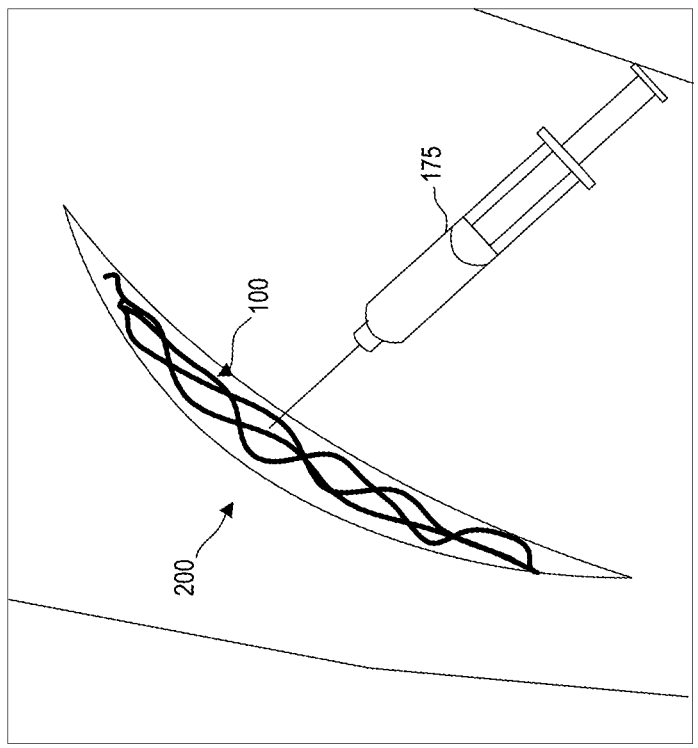

FIGS. 2A and 2B illustrate an example of applying an opioid independent surgical anesthetic composition to a surgical site 200 (e.g., on an appendage of a human or animal subject). In particular, FIG. 2A illustrates the syringe 175 from FIGS. 1A-1B loaded with lipid matrix particle HALA 100, where the syringe 175 is being used to topically apply the lipid matrix particle HALA 100 over the surgical site 200.

As noted hereinabove, although hyaluronic acid hydrogels exhibit a gel-like consistency (similar to hair gel), hyaluronic acid hydrogels also exhibit shear-thinning mechanical properties, enabling the lipid matrix particle HALA 100 to be injectable through the needle of the syringe 175 (e.g., 18 G-25 G). After passing through the needle of the syringe 175, the lipid matrix particle HALA 100 reforms into a stable gel. Because of its viscosity, in some instances, the lipid matrix particle HALA 100 gel remains where initially applied over the surgical site 200. For example, the hydrogel may have a viscosity greater than 1000 cps, greater than 3000 cps, greater than 5000 cps, or greater than 10,000 cps (e.g., at low or no shear).

FIG. 2B illustrates the surgical site 200 of FIG. 2A, where the surgical site 200 has been closed (e.g., via suture 205). Upon closing the surgical site/wound, the lipid matrix particle HALA 100 intercalates within natural crevices of the surgical site 200 and smears between compressed tissues. The hydrogel of the lipid matrix particle HALA 100 serves to physically sequester the bupivacaine, ropivacaine, or other anesthetic-loaded lipid matrix particles, temporarily shielding them from surrounding in vivo environment. The hydrogel serves to conceal the lipid matrix particles from the immediate in vivo environment and slows the degradation and removal of the anesthetic drug load from the lipid matrix particle HALA 100 into the surgical wound region, therefore allowing the natural prolonged release of the anesthetic. The formulation will be naturally absorbed by the body over time.

Accordingly, a lipid matrix particle HALA 100 of the present disclosure may be applied in a simple manner (e.g., topical application, as shown in FIG. 2A), avoiding complicated and/or repetitive injection and/or admixing procedures (sometimes involving multiple syringes for treating both immediate postoperative pain and lingering postoperative pain) associated with conventional products that attempt to provide long-acting local anesthetic effects.

Figure 3:
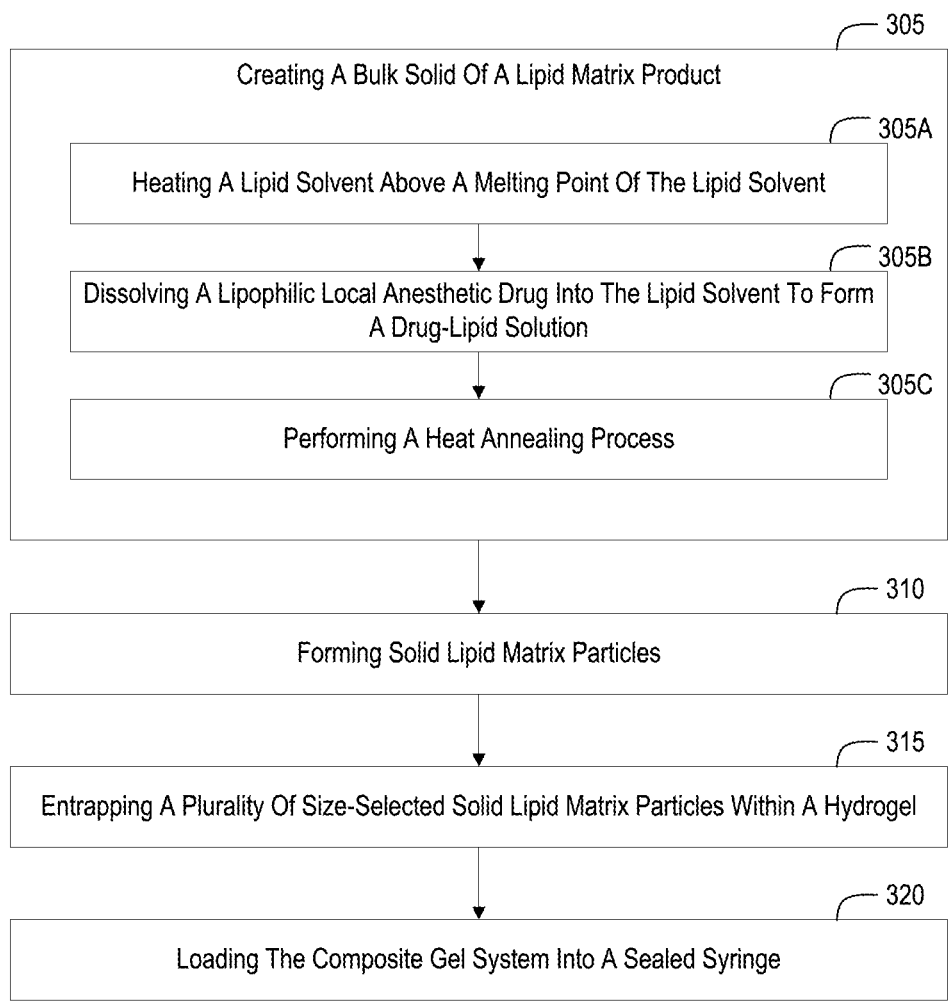
FIG. 3 illustrates an example flow diagram depicting acts associated with creating an opioid independent surgical anesthetic composition, in accordance with one or more embodiments of the present disclosure.

Some embodiments of the present disclosure can also be described in terms of acts (e.g., acts of a method) for accomplishing a particular result. Along these lines, FIG. 3 illustrates an example flow diagram 300 depicting acts associated with creating an opioid independent surgical anesthetic composition (e.g., a lipid matrix particle HALA 100). Although the acts shown in flow diagram 300 may be illustrated and/or discussed in a certain order, no particular ordering is required unless specifically stated or required because an act is dependent on another act being completed prior to the act being performed.

In some instances, the acts of the flow diagrams are described below with reference to the systems, components, structures, and/or elements of FIGS. 1A-1B. For instance, at least some reference numerals included parenthetically hereinbelow refer, by way of illustrative example, to systems, components, structures, and/or elements described hereinabove with reference to FIGS. 1A-1B.

Act 305 of flow diagram 300 includes creating a bulk solid of a lipid matrix product (145). Creating a bulk solid of a lipid matrix product can itself include various sub-acts. For example, act 305A includes heating a lipid solvent above a melting point of the lipid solvent. In some instances, the lipid solvent includes a saturated triglyceride (130), such as tristearin with a melting point of approximately 72.5° C. Lipid blends of glycerides may also be used (e.g., a blend of saturated mono, di, and/or triglycerides). Act 305B includes dissolving a lipophilic local anesthetic drug into the lipid solvent to form a drug-lipid solution. In some implementations, the lipophilic local anesthetic drug comprises freebase bupivacaine, ropivacaine (125) or another amide based local anesthetic.

Between act 305B and act 305C the process can include reducing a temperature of the drug-lipid solution to below the melting point of the lipid solvent, thereby forming the bulk solid of the lipid matrix product. Such an act may include quickly quenching the drug-lipid solution to ambient temperature (e.g., about 20° C. to 25° C.) or below. After such quenching, a heat annealing process noted at 305 C may be performed. The heat annealing process may include maintaining a temperature of the drug-lipid solution at approximately 8° C.-12° C. below the melting point of the lipid solvent for a period of time (e.g., one hour or longer, such as 2 hours). For example, where the lipid solvent comprises tristearin, a heat annealing process may include maintaining a temperature of the drug-lipid solution at 62° C. for a time period of 2 hours. Where a lipid blend is employed, the heat annealing may be configured to maintain the temperature at 8° C. to 12° C. below the melting point of a given glyceride of the blend (e.g., the glyceride with the highest melting point).

Act 310 of flow diagram 300 includes forming solid lipid matrix particles (105). In some instances, forming the solid lipid matrix particles (105) includes crushing or pulverizing the bulk solid of the lipid matrix product (145) (e.g., with a mortar and pestle or device of similar functionality). In some instances, the solid lipid matrix particles (105) may be sieved to isolate the solid lipid matrix particles (105) into different size ranges.

Act 315 of flow diagram 300 includes entrapping a plurality of size-selected solid lipid matrix particles (105) within a hydrogel (110). In some embodiments, as described above, the size-selected solid lipid matrix particles (105)

have a longest dimension that is between about 25 µm-500 µm, preferably between about 50 µm-300 µm, more preferably about 200 µm or less (e.g., 25 µm or smaller, between 25 µm and 50 µm, between 100 µm and 125 µm, etc.). The hydrogel (110) may comprise a cross-linked or non-cross-linked hyaluronic acid hydrogel.

Act 320 of flow diagram 300 includes loading the composite gel system (lipid matrix particle HALA 100) into a sealed syringe (175). The shear-thinning properties of the composite gel system may facilitate injectability of the composite gel system through the syringe (175), providing a convenient and simple mechanism for delivery of the composite gel system to a treatment site.

Figure 4:
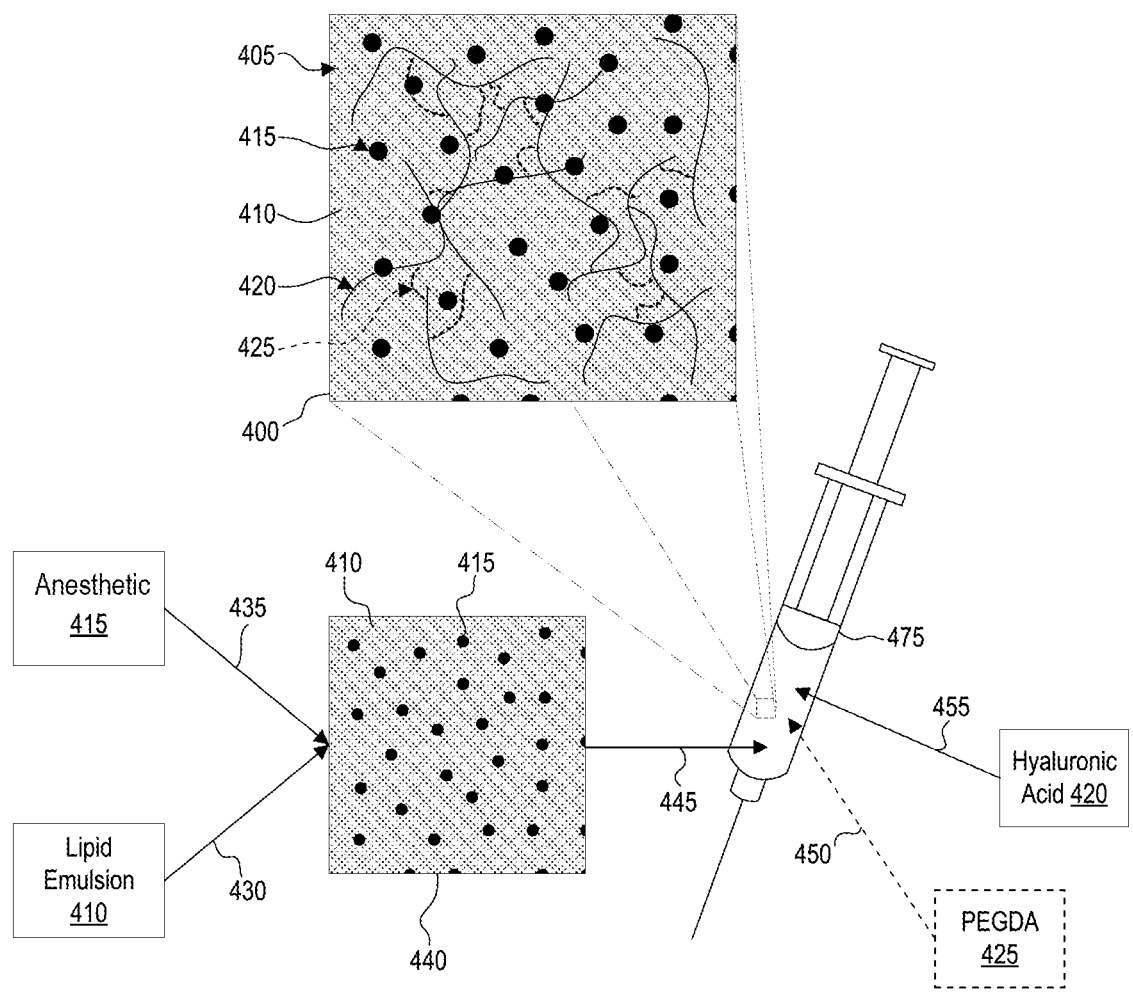
FIG. 4 illustrates a schematic representation of an alternative embodiment of an opioid independent surgical anesthetic composition that includes a hydrogel that entraps lipid emulsion droplets containing the amide based anesthetic entrained therein and a schematic representation of a procedure for manufacturing the opioid independent surgical anesthetic composition, in accordance with one or more embodiments of the present disclosure.

FIG. 4 illustrates a schematic representation of an alternative embodiment of an opioid independent surgical anesthetic composition (i.e., lipid emulsion HALA 400). FIG. 4 illustrates that the lipid emulsion HALA 400 includes a hydrogel 405 that entraps lipid emulsion droplets 410 containing bupivacaine, ropivacaine, or other anesthetic 415 entrained therein. Similar to the hydrogel 110 described hereinabove with reference to FIGS. 1A-1B, the hydrogel 405 of the lipid emulsion HALA 400 may comprise hyaluronic acid 420. A cross-linker 425 may or may not be present. The hydrogel 405 may shield at least some of the lipid emulsion droplets 410 that contain ropivacaine, bupivacaine or other anesthetic 415 entrained therein from harsh in vivo conditions, thereby facilitating a controlled, prolonged release of anesthetic 415 from the lipid emulsion HALA 400 into a surgical or injection site.

FIG. 4 also illustrates a schematic representation of a procedure for manufacturing the lipid emulsion HALA 400. As depicted in FIG. 4, freebase ropivacaine, bupivacaine or other anesthetic 415 may be mixed with a lipid emulsion 410, indicated in FIG. 4 by arrows 430 and 435. In one example, the lipid emulsion 410 may comprise Intralipid® 20%, an FDA approved parenteral nutrition lipid emulsion that includes 20% soybean oil, 1.2% egg yolk phospholipids, and 2.25% glycerin. The mixture may be homogenized using a homogenizer (e.g., using high-speed homogenization, high-pressure homogenization, sonication, microfluidic homogenization, and/or other techniques), resulting in an anesthetic-loaded emulsion 440 that comprises lipid emulsion droplets 410 that contain ropivacaine, bupivacaine or other anesthetic 415 loaded therein.

The anesthetic-loaded emulsion 440 may then be mixed with components for forming the hydrogel 405 (e.g., hyaluronic acid 420, optionally a crosslinker such as PEGDA 425; mixing indicated in FIG. 4 by arrows 445, 450, and 455). Similar to the lipid matrix particle HALA 100 described hereinabove with reference to FIGS. 1A-1B, the mixed anesthetic-loaded emulsion 440, and hyaluronic acid 420 may be disposed within a syringe 475, providing a lipid emulsion HALA 400 that is ready for immediate use by a medical practitioner in a manner that avoids bedside admixing or other complicated procedures.

The lipid emulsion HALA 400 may be administered to a treatment site in a manner that is similar to those described hereinabove for the lipid matrix particle HALA 100 (e.g., see FIGS. 2A and 2B). Furthermore, drug release characteristics of a lipid emulsion HALA 400 may be customized by modifying various components, such as homogenization parameters (e.g., pressure, cycles, phospholipid content, etc.), % amount of lipids used, drug load concentration, type and/or degree and/or mass ratio of crosslinking, and/or others.

The various components of the composition may be included in any appropriate amount. By way of example, in an embodiment, the hyaluronic acid is included in an amount of at least 0.5%, such as from 0.5% to 3%, from 1% to 2.5%, or from 1.5 to 2.3% by weight. The molecular weight (e.g., weight average molecular weight or number average molecular weight, but typically weight average molecular weight) of the hyaluronic acid may be at least 500,000 Da, such as from 500,000 to 3,000,000 Da, from 1,000,000 to 3,000,000 Da, or from 1,500,000 to 2,750,000 Da.

In an embodiment, the local anesthetic drug has a concentration relative to the solid matrix lipid particles in which it is included of at least 1% such as from 1% to 50%, from 5% to 40%, or from 10% to 30% by weight of the particles. The remainder of the particle may be made up of the lipid or lipid blend matrix (e.g., 50-99%, 60-95%, or 70-90%).

In an embodiment, the concentration of the local anesthetic drug relative to the composition as a whole may be at least 0.5%, such as from 0.5% to 10%, from 1% to 5%, or from 2% to 4% by weight of the overall composition. Both the concentration of drug in the lipid particles, and the overall concentration in the formulation as a whole can be important. The first describes how much drug and lipid are included in the lipid matrix particles. Additionally, the drug release profile can be tuned via this parameter (e.g., lower drug loading equals slower release, and higher drug loading equals quicker and larger burst release). The second equates to the final dosage form and is related to its clinical use, and will of course be important to the clinician and user, to know how much drug is being applied overall.

Another route available to increase drug loading of the final composition without necessarily increasing the lipid particle drug loading is to increase the amount of particles loaded into each mL of composition, in other words, increasing the particle density within the composition as a whole. In an embodiment, the composition may include the solid lipid matrix particles at a density within the composition as a whole that is at least 25 mg/mL, such as from 25 mg/mL to 300 mg/mL, from 50 mg/mL to 200 mg/mL, or from 100 mg/mL to 175 mg/mL.

EXAMPLES

The following examples as set forth herein are intended for illustrative purposes only and are not intended to limit the scope of the disclosure in any way. Rather, the examples are intended to demonstrate one or more aspects and/or advantages of the opioid independent surgical anesthetics disclosed herein.

Example 1

Figure 5:
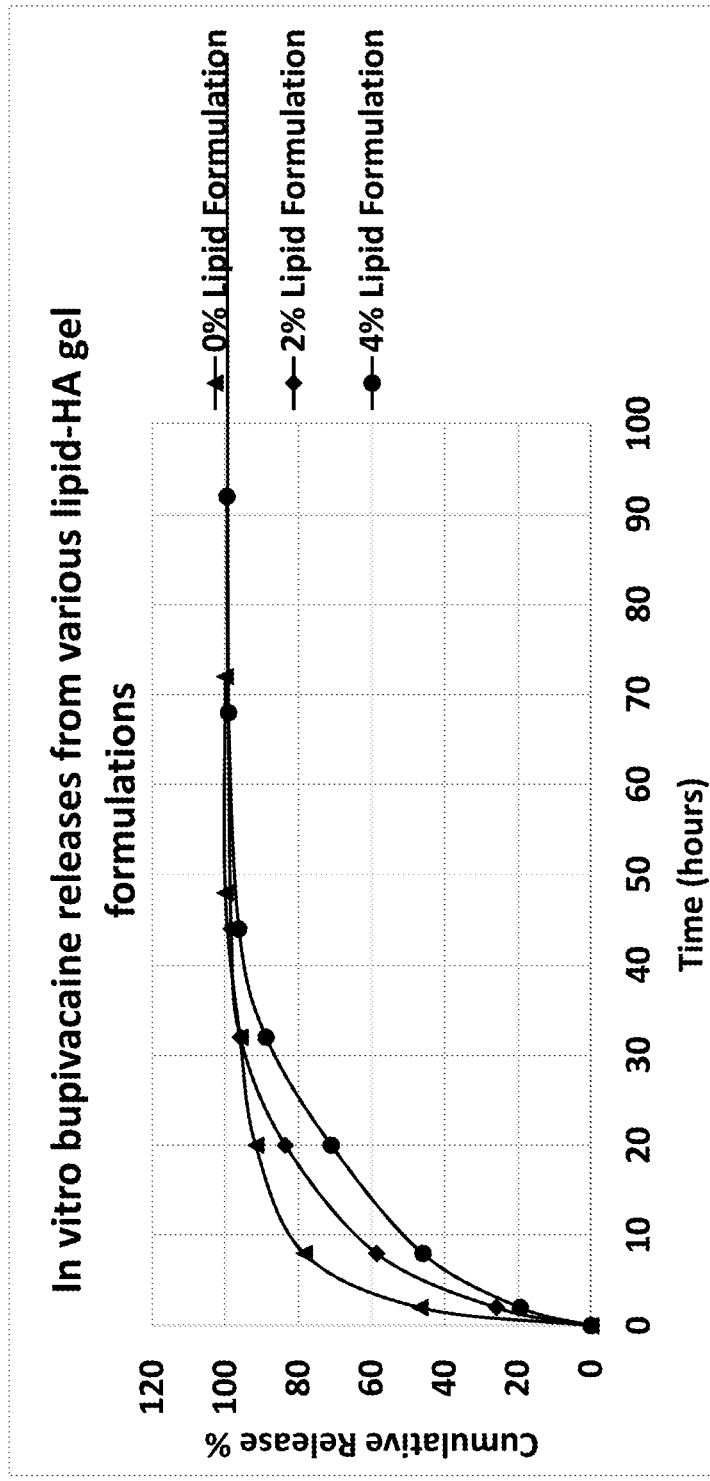
FIG. 5 illustrates a graph of in vitro data of cumulative bupivacaine release over time from various lipid-HA (hyaluronic acid) gel formulations (i.e., opioid independent surgical anesthetic compositions that include hyaluronic acid hydrogels that have lipid emulsion droplets containing bupivacaine entrained therein, such as the opioid independent surgical anesthetic composition of FIG. 4, which can also be referred to herein as lipid emulsion hyaluronic acid local anesthetic (HALA) or hyaluronic acid bupivacaine-loaded emulsion (HA-BLE) composite gel)

FIG. 5 illustrates a graph of in vitro data of cumulative bupivacaine release over time from various lipid-HA (hyaluronic acid) gel formulations. Some of the lipid-HA gel formulations represented in FIG. 5 correspond to the lipid emulsion HALA formulations described hereinabove with reference to FIG. 4. FIG. 5 includes data for a 0% lipid HA gel formulation, a 2% lipid emulsion HALA, and a 4% lipid emulsion HALA.

As is evident from FIG. 5, the illustrated lipid emulsion HALA formulations are configured to release bupivacaine in a biphasic manner (i.e., an initial high release rate burst phase followed by a low release rate sustained release phase). For example, the various HALA formulations represented in FIG. 5 released a significant portion of bupivacaine (e.g., to achieve a cumulative release % within a range of about 30%-70%) during an initial burst phase within a range of about 8-24 hours post administration.

Following the burst phase, the various HALA formulations released an additional significant amount of bupivacaine following the initial burst phase (e.g., to achieve a cumulative release % within a range of about 70%-99%) during a sustained release phase (e.g., from the end of the burst phase to about 72 hours or more post administration).

A comparison of the cumulative release profiles of the various HALA formulations represented in FIG. 5 indicates that drug release from a HALA is modifiable based on the amount of lipids used in the HALA formulation. For example, the 4% lipid formulation of FIG. 5 achieved drug release at a lower rate during the burst phase than the 2% or 0% lipid formulations, saving more of the anesthetic for the sustained release phase, by comparison.

The results illustrated in FIG. 5 underscore the tunability of temporal anesthetic release in burst and sustained release phases, which enable the lipid emulsion HALA formulations of the present disclosure to address both acute postoperative pain (e.g., via initial burst drug release) as well as lingering pain experienced as a surgical site heals (e.g., via sustained drug release following the burst release). Although prepared using bupivacaine, it will be appreciated the ropivacaine or another amide based anesthetic could be used.

Example 2

Figures 6A, 6B:
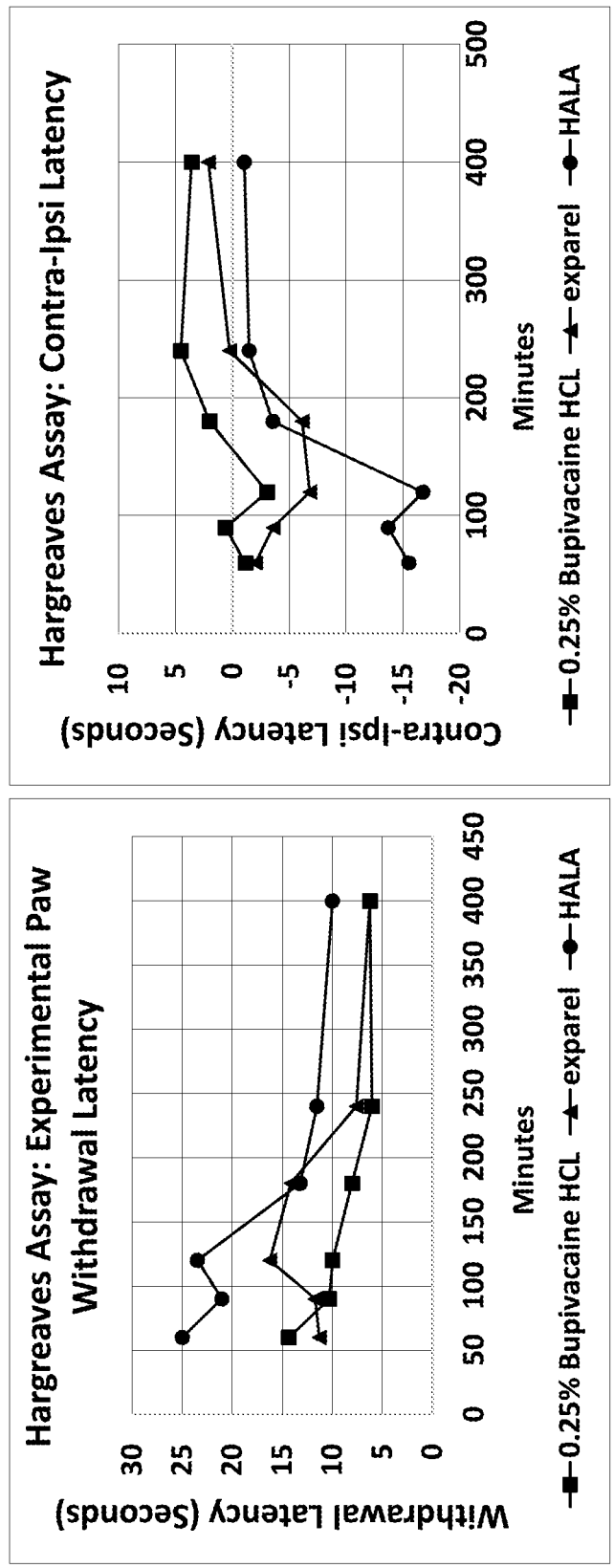
FIGS. 6A and 6B illustrate graphs of in vivo data of paw withdrawal latency and contralateral-ipsilateral latency for rodents treated with a lipid emulsion HALA.

FIGS. 6A and 6B illustrate graphs of in vivo data of paw withdrawal latency and contra-ipsi latency for rodents treated with a lipid emulsion HALA. The data represented in the graphs of FIGS. 6A and 6B were obtained according to the Hargreaves Assay, which is a standardized rodent thermal nociception assay that assesses a rodent's paw withdrawal latency after application of a thermal stimulus. Bupivacaine HCL and Exparel® were delivered via injections into tissue adjacent to the sciatic nerve. Lipid emulsion HALA gel was administered via infiltration into the sciatic nerve cavity. Paw withdrawal latency was measured after application of a thermal stimulus to the injured paw. As is evident from FIG. 6A, the lipid emulsion HALA group had generally higher paw withdrawal latencies than both the bupivacaine HCL and Exparel®, indicating greater anesthetic effect from the lipid emulsion HALA group. Furthermore, FIG. 6B illustrates contralateral-ipsilateral latencies measured for rodents treated with bupivacaine HCL, Exparel®, and lipid emulsion HALA, as described above. As is evident from FIG. 6B, the lipid emulsion HALA group had generally lower paw contralateral-ipsilateral latencies than both the bupivacaine HCL and Exparel®, indicating greater anesthetic effect from the lipid emulsion HALA group. Although conducted using bupivacaine, it will be appreciated the ropivacaine or another amide based anesthetic could be used.

Example 3

Figure 7:
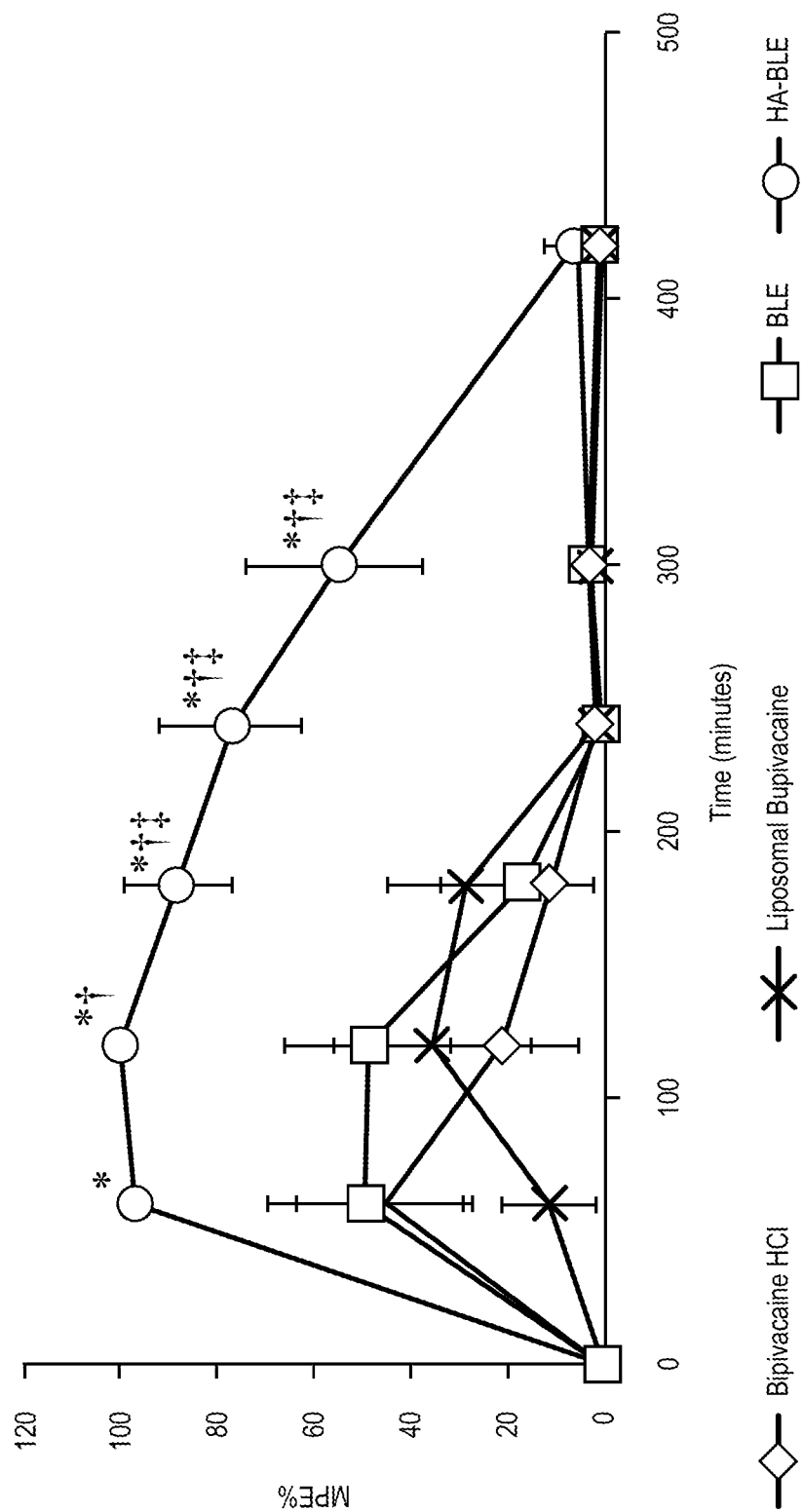
FIG. 7 illustrates a graph of in vivo data showing the maximum possible effect (MPE %) of anesthetic in a thermal nociceptive assay for bupivacaine-loaded emulsions (BLE) and HA-BLE compared to controls of bupivacaine HCL and liposomal bupivacaine.

FIG. 7 illustrates a graph of in vivo data showing the maximum possible effect (MPE) % of anesthetic in a thermal nociceptive assay for bupivacaine-loaded emulsions (BLE) (without a hyaluronic acid hydrogel carrier) and HA-BLE (corresponding to lipid emulsion HALA, described hereinabove) compared to controls of bupivacaine HCL and liposomal bupivacaine. A rat sciatic nerve block model and thermal nociceptive assay was used to compare the anesthetic effect of the compositions described above. As is evident from FIG. 7, HA-BLE produced a significantly greater anesthetic effect and duration compared to Exparel® (liposomal bupivacaine) and 0.25% bupivacaine HCL, alone. Although conducted using bupivacaine, it will be appreciated the ropivacaine or another amide based anesthetic could be used.

Example 4

Figure 8:
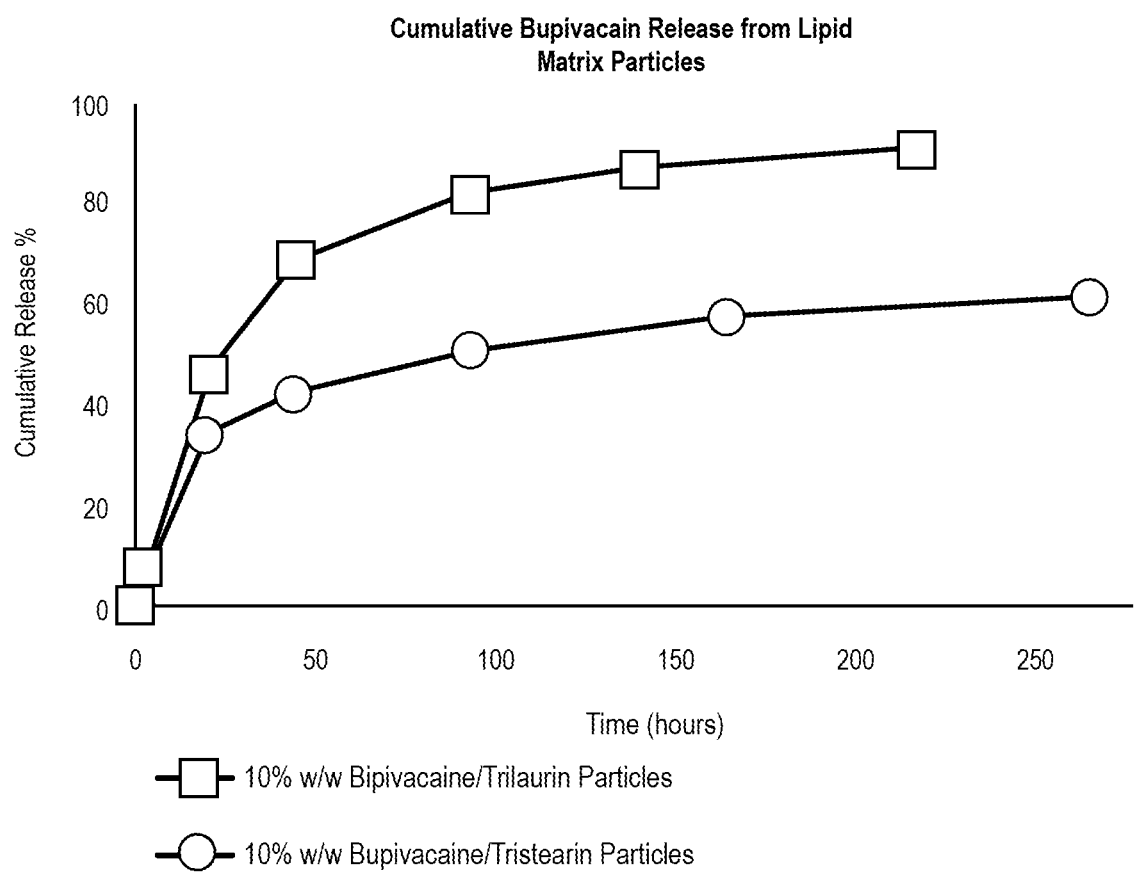
FIG. 8 illustrates a graph of cumulative bupivacaine release over time from various HA hydrogel formulations that include bupivacaine-loaded lipid matrix particles (i.e., opioid independent surgical anesthetic compositions that include solid lipid matrix particles entrapped within a hyaluronic acid hydrogel, such as the opioid independent surgical anesthetic composition of FIG. 1A)
Figure 9:
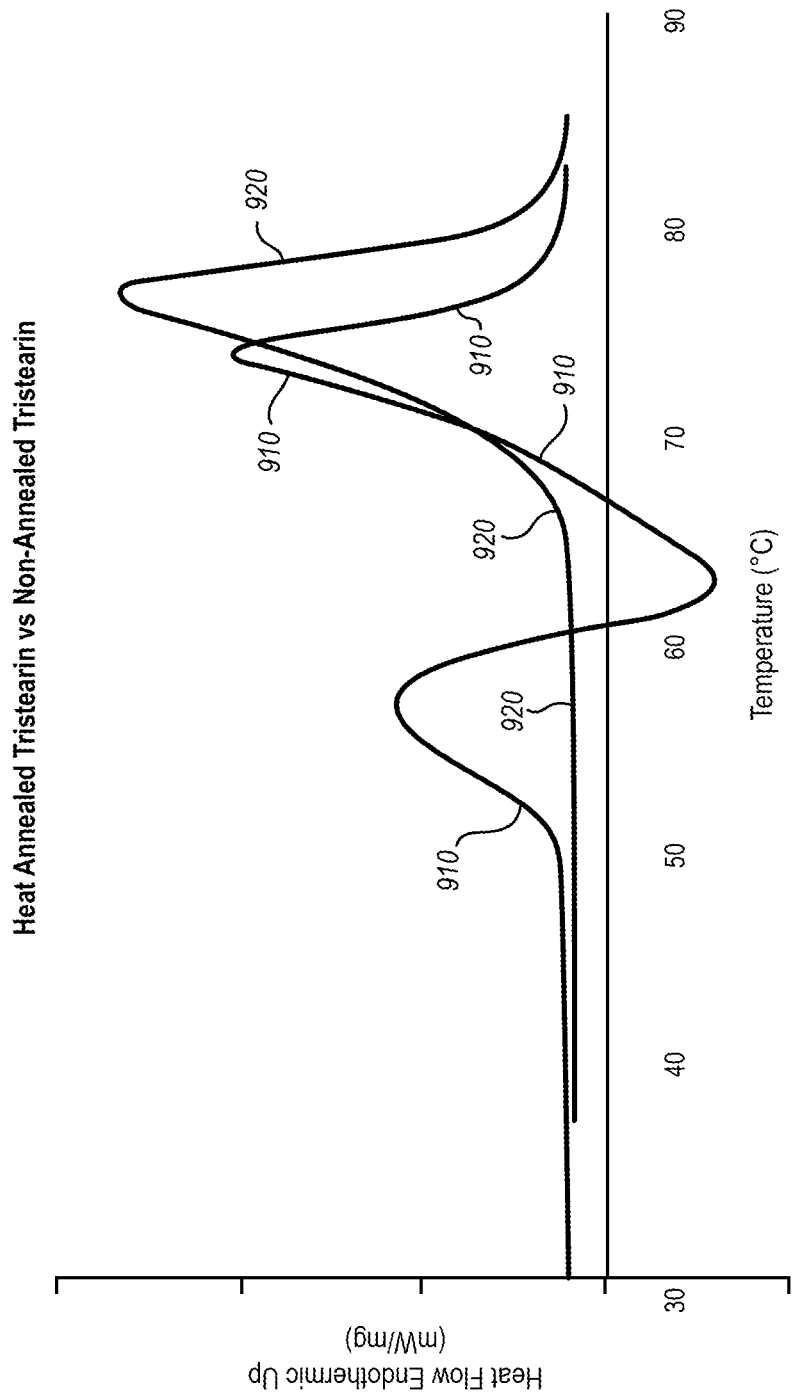
FIG. 9 illustrates a graph of differential scanning calorimetry data of heat annealed bupivacaine-loaded lipid matrix particles and non-annealed bupivacaine-loaded lipid matrix particles, in accordance with one or more embodiments of the present disclosure.

FIG. 8 illustrates a graph of cumulative bupivacaine release over time from various HA hydrogel formulations that include bupivacaine-loaded lipid matrix particles (i.e., lipid matrix particle HALA, as described hereinabove with reference to FIGS. 1-3). In particular, FIG. 8 illustrates bupivacaine release profiles for a lipid matrix particle HALA formed with trilaurin and for a lipid matrix particle HALA formed with tristearin (having a longer triglyceride chain than trilaurin).

Similar to the lipid emulsion HALA formulations represented in FIG. 5, the lipid matrix particle HALA compositions represented in FIG. 8 demonstrate controlled release of bupivacaine, in particular in an initial burst phase and a subsequent sustained release phase. The sustained release phases for the lipid matrix particle HALA compositions of FIG. 8 appear to extend for longer periods of time than the sustained release phases of the lipid emulsion HALA compositions of FIG. 5, indicating that lipid matrix particle HALA compositions show promise for effectuating long-acting anesthetic effects to combat postoperative pain.

Furthermore, as is evident from FIG. 8, the lipid matrix particle HALA formed with tristearin appears to have a significantly slower drug release profile than the lipid matrix particle HALA formed with trilaurin, indicating that the triglyceride chain length selected to form solid lipid matrix particles may influence the drug release characteristics of the lipid matrix particle HALAs. It will be appreciated that the chain lengths for the lipid chains need not be identical, across all three glyceride linkages, providing further ability to tailor the anesthetic release profile as desired. Although conducted using bupivacaine, it will be appreciated the ropivacaine or another amide based anesthetic could be used.

Accordingly, at least some HALAs of the present disclosure are configured to provide a high-rate burst drug release upon administration to a surgical site followed by a low-rate prolonged drug release. In this regard, a HALA of the present disclosure may address both acute pain that immediately follows a surgical procedure as well as lingering pain experienced as a surgical site heals and have the potential to reduce or eliminate dependence on systemic opioids as a method for postoperative pain management.

Although principally described in the context of delivery of ropivacaine, bupivacaine, or another amide based anesthetic, the present embodiments may also find use for delivery of other drugs or actives, e.g., with a solid-lipid matrix particles including such an active, in a hydrogel.

The compositions described herein may advantageously be applied topically (e.g., to a desired wound bed), as described herein. Alternatively, administration through injection via various routes may also be possible. Examples of such injection sites include, but are not limited to, the intrathecal space, intra-articular space, and other fluid-filled cavities as well as transdermal, oral, sub-cutaneous, intranasal, vaginal, buccal, epidural, ocular space, dental, intratumoral, intramuscular, or intravenous injectable delivery of the composition on its own or in combination with another therapeutic agent.

It is to be understood that features described with regard to the various embodiments herein may be mixed and matched in any desired combination. In addition, the concepts disclosed or envisioned herein may be embodied in other specific forms. The described embodiments are to be considered in all respects only as illustrative and not restrictive. The scope is, therefore, indicated by the appended claims rather than by the foregoing description. All changes which come within the meaning and range of equivalency of the claims are to be embraced within their scope.

What is claimed is:

1. An opioid independent surgical anesthetic composition, comprising an injectable dosage form of a gel having a plurality of solid lipid matrix particles entrapped therein, the plurality of solid lipid matrix particles comprising a lipophilic local anesthetic drug and a saturated glyceride, wherein the injectable dosage form is shear thinning and is injectable through an 18 to 25 gauge needle, wherein the injectable dosage reforms into a stable gel after passing through the 18 to 25 gauge needle, and wherein the composition is biphasic so as to release the local anesthetic drug in a biphasic manner when administered at a surgical site, the biphasic release comprising an initial burst phase followed by a sustained release phase.

2. The composition of claim 1, wherein the saturated glyceride comprises a lipid blend including one or more of a monoglyceride, a diglyceride, or a triglyceride.

3. The composition of claim 1, wherein the saturated glyceride comprises a saturated triglyceride.

4. The composition of claim 1, wherein the gel comprises a hyaluronic acid hydrogel.

5. The composition of claim 4, wherein the hyaluronic acid is included in an amount from 0.5% to 3% by weight.

6. The composition of claim 4, wherein the hyaluronic acid has a molecular weight in a range from 500,000 to 3,000,000 Da.

7. The composition of claim 1, wherein the lipophilic local anesthetic drug comprises at least one amide based anesthetic.

8. The composition of claim 1, wherein the plurality of solid lipid matrix particles substantially comprises triglycerides forming a β-phase crystalline state.

9. The composition of claim 1, wherein the solid lipid matrix particles have a melting point greater than about 45° C.

10. The composition of claim 1, wherein the solid lipid matrix particles are comprised of one or more of monoglycerides, diglycerides, or triglycerides with carbon chain lengths of 12 to 22 carbon atoms.

11. The composition of claim 1, wherein each of the plurality of solid lipid matrix particles has a longest dimension of about 200 μm or less.

12. The composition of claim 1, wherein the local anesthetic drug has a concentration relative to the solid matrix lipid particle of from 1% to 50% by weight.

13. The composition of claim 1, wherein the local anesthetic drug has a concentration relative to the composition as a whole that is from 0.5% to 10% by weight.

14. The composition of claim 1, wherein the solid lipid matrix particles have a density within the composition as a whole that is from 25 mg/mL to 300 mg/mL.

15. An opioid independent surgical anesthetic composition as recited in claim 1, wherein the composition consists essentially of the injectable dosage form that is ready-to-use, the composition being a hyaluronic acid hydrogel having a liposomal emulsion containing bupivacaine, ropivacaine, lidocaine, or another amide based local anesthetic entrained therein.

16. The composition of claim 15, wherein the biphasic composition releases bupivacaine, ropivacaine, lidocaine, or another amide based local anesthetic in a biphasic manner when administered at a surgical site, the biphasic release comprising a burst phase and a sustained release phase, wherein:
(i) between 30%-70% of the bupivacaine, ropivacaine, lidocaine, or another amide based local anesthetic is cumulatively released from the hydrogel during the burst phase between 8-24 hours post administration, and/or
(ii) between 70%-99% of the bupivacaine, ropivacaine, lidocaine, or another amide based local anesthetic is cumulatively released from the hydrogel by 72 hours post administration.

17. The composition of claim 1, wherein the solid lipid matrix particles have a melting point greater than about 70° C.

18. The composition of claim 1, wherein the solid lipid matrix particles consist essentially of bupivacaine in tristearin.

19. The composition of claim 1, wherein the solid lipid matrix particles consist of bupivacaine in tristearin.

20. An opioid independent surgical anesthetic composition packaged within a syringe, the composition comprising an injectable dosage form of a gel having a plurality of solid lipid matrix particles entrapped therein, the plurality of solid lipid matrix particles comprising a lipophilic local anesthetic drug comprising bupivacaine, in tristearin as the solid lipid matrix, wherein the injectable dosage form is shear thinning and is injectable through an 18 to 25 gauge needle attached to the syringe, and wherein the injectable dosage reforms into a stable gel after passing through the 18 to 25 gauge needle;
wherein the composition consists essentially of the injectable dosage form that is ready-to-use provided within the syringe with an attached 18 to 25 gauge needle;
wherein the composition is biphasic so as to release the bupivacaine in a biphasic manner when administered at a surgical site, the biphasic release comprising an initial burst phase and a sustained release phase, wherein:
(i) between 30%-70% of the bupivacaine is cumulatively released from the gel during the burst phase between 8-24 hours post administration; and
(ii) between 70%-99% of the bupivacaine is cumulatively released from the gel by 72 hours post administration.

21. The composition packaged within a syringe of claim 20, wherein the bupivacaine has a concentration relative to the solid matrix lipid particle of from 1% to 50% by weight.

22. An opioid independent surgical anesthetic composition, comprising an injectable dosage form of a gel having a plurality of solid lipid matrix particles entrapped therein, the plurality of solid lipid matrix particles consisting of an oil and bupivacaine in tristearin, wherein the injectable dosage form is shear thinning to facilitate injection through an 18 to 25 gauge needle and wherein the composition is configured to release the bupivacaine in a biphasic manner when administered at a surgical site, the biphasic release comprising an initial burst phase followed by a sustained release phase.

23. An opioid independent surgical anesthetic composition, comprising an injectable dosage form of a gel having a plurality of lipid matrix particles disposed therein, the plurality of lipid matrix particles consisting of a lipophilic local anesthetic drug, an oil, and a saturated triglyceride, wherein the injectable dosage form is shear thinning and is injectable through an 18 to 25 gauge needle and wherein the composition is biphasic so as to release the local anesthetic drug in a biphasic manner when administered at a surgical site, the biphasic release comprising an initial burst phase followed by a sustained release phase.

* * * * *